(12) United States Patent
Atlas

(10) Patent No.: US 8,530,407 B2
(45) Date of Patent: Sep. 10, 2013

(54) MULTI-COMPONENT ANTIOXIDANT COMPOUNDS, PHARMACEUTICAL COMPOSITIONS CONTAINING SAME AND THEIR USE FOR REDUCING OR PREVENTING OXIDATIVE STRESS

(75) Inventor: Daphne Atlas, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 13/455,155

(22) Filed: Apr. 25, 2012

(65) Prior Publication Data
US 2012/0264676 A1 Oct. 18, 2012

Related U.S. Application Data

(63) Continuation of application No. 13/086,429, filed on Apr. 14, 2011, now abandoned, which is a continuation of application No. 11/797,590, filed on May 4, 2007, now abandoned, which is a continuation of application No. 10/234,319, filed as application No. PCT/IL01/00984 on Oct. 25, 2001, now abandoned.

(30) Foreign Application Priority Data

Oct. 26, 2000 (GB) .................................. 0026254.3

(51) Int. Cl.
*A61P 11/06* (2006.01)
*A61K 38/00* (2006.01)

(52) U.S. Cl.
USPC ........................................................ 514/1.7

(58) Field of Classification Search
None
See application file for complete search history.

(56) References Cited

U.S. PATENT DOCUMENTS

| | | | |
|---|---|---|---|
| 4,738,841 A | 4/1988 | Pigiet | |
| 4,966,848 A | 10/1990 | Smith et al. | |
| 5,223,421 A | 6/1993 | Smith et al. | |
| 5,464,825 A | 11/1995 | Anderson et al. | |
| 5,683,982 A | 11/1997 | McLean et al. | |
| 5,837,218 A | 11/1998 | Peers et al. | |
| 5,869,615 A | 2/1999 | Hourcade et al. | |
| 5,874,468 A | 2/1999 | Atlas et al. | |
| 5,906,811 A | 5/1999 | Hersh | |
| 5,985,261 A | 11/1999 | White et al. | |
| 6,031,077 A | 2/2000 | Klimowski et al. | |
| 6,686,443 B1 | 2/2004 | Rabenstein et al. | |
| 2003/0109457 A1 | 6/2003 | Atlas | |
| 2007/0287662 A1 | 12/2007 | Atlas | |

FOREIGN PATENT DOCUMENTS

| EP | 0354820 | | 2/1990 |
|---|---|---|---|
| EP | 486921 A1 | * | 11/2001 |
| GB | 2368339 | | 5/2002 |
| WO | WO 97/10266 | | 3/1997 |
| WO | WO 97/14430 | | 4/1997 |
| WO | WO 98/29375 | | 7/1998 |
| WO | WO 99/50286 | | 10/1999 |
| WO | WO 02/18369 | | 3/2002 |
| WO | WO 02/34202 | | 5/2002 |

OTHER PUBLICATIONS

Communication Pursuant to Article 94(3) EPC Dated Mar. 1, 2010 From the European Patent Office Re.: Application No. 01980877.3.
Communication Pursuant to Article 94(3) EPC Dated Jun. 2, 2008 From the European Patent Office Re.: Application No. 01980877.3.
Office Action Dated Feb. 14, 2008 From the Israeli Patent Office Re.: Application No. 155497.
Official Action Dated Mar. 3, 2010 From the US Patent and Trademark Office Re.: U.S. Appl. No. 11/797,590.
Official Action Dated Feb. 5, 2007 From the US Patent and Trademark Office Re.: U.S. Appl. No. 10/234,319.
Official Action Dated Aug. 9, 2006 From the US Patent and Trademark Office Re.: U.S. Appl. No. 10/234,319.
Official Action Dated Jun. 9, 2010 From the US Patent and Trademark Office Re.: U.S. Appl. No. 11/797,590.
Official Action Dated Jul. 19, 2011 From the US Patent and Trademark Office Re. U.S. Appl. No. 13/086,429.
Official Action Dated Dec. 21, 2010 From the US Patent and Trademark Office Re.: U.S. Appl. No. 11/797,590.
Official Action Dated Nov. 25, 2011 From the US Patent and Trademark Office Re. U.S. Appl. No. 13/086,429.
Official Action Dated Jan. 30, 2006 From the US patent and Trademark Office Re.: U.S. Appl. No. 10/234,319.
Requisition by the Examiner Dated Feb. 24, 2009 From the Canadian Intellectual Property Office Re.: Application No. 2,427,005.
Response Dated May 3, 2010 to Official Action of Mar. 3, 2010 From the US Patent and Trademark Office Re.: U.S. Appl. No. 11/797,590.
Response Dated Dec. 9, 2008 to Communication Pursuant to Article 94(3) EPC of Jun. 2, 2008 From the European Patent Office Re.: Application No. 01980877.3.
Response Dated Oct. 12, 2010 to Official Action of Jun. 9, 2010 From the US Patent and Trademark Office Re.: U.S. Appl. No. 11/797,590.
Response Dated Sep. 19, 2011 to Official Action of Jul. 19, 2011 From the US Patent and Trademark Office Re. U.S. Appl. No. 13/086,429.
Supplementary European Search Report Dated Aug. 28, 2007 From the European Patent Office Re.: Application No. 01980877.3.
Translation of Notice of Reason for Rejection Dated Apr. 13, 2007 From the Japanese Patent Office Re.: Applicaiton No. 2002-537256.

(Continued)

*Primary Examiner* — Thomas Heard

(57) ABSTRACT

An antioxidant compound is disclosed, along with pharmaceutical compositions and methods of treatment which utilize said compound. The compound is characterized by a peptide including at least three amino acid residues of which at least two are cysteine residues, and a first hydrophobic or non-charged moiety being attached to an amino terminal of the peptide via a first bond and a second hydrophobic or non-charged moiety being attached to a carboxy terminal of the peptide via a second bond, as described herein. Cleavage of the peptide by an intracellular peptidase results in generation of a plurality of antioxidant species, each including one of the cysteine residues, thereby providing for a plurality of different antioxidant species acting in synergy in exerting antioxidation.

6 Claims, 2 Drawing Sheets

(56) References Cited

OTHER PUBLICATIONS

Translation of Official Decision of Rejection Dated Jan. 4, 2008 From the Japanese Patent Office Re.: Application No. 2002-537256.
Akaike "Role of Free Radicals in Viral Pathogenesis and Mutation", Reviews in Medical Virology, 11(2): 87-101, 2001.
Bartov et al. "Low Molecular Weight Thiol Amides MAPK Activity and Protect Primary Neurons From A?(1-42) Toxicity", Brain Research, 1069: 198-206, 2006.
Brown et al. "Role of Microglia and Host Prion Protein in Neurotoxicity of a Prion Protein Fragment", Nature, 380(6572): 345-347, 1996.
Bundy et al. "Synthesis of Novel 2,4-Diaminopyrrolo-[2,3-D]Pyrimidincs With Antioxidant, Neuroprotective, and Antiasthma Activity", Journal of Medicinal Chemistry, 38(21): 4161-4163, 1995.
Buttke et al. "Oxidative Stress as a Mediator of Apoptosis", Immunology Today, 15 (1): 7-10, 1994.
Cafe et al. "Oxidative Stress After Acute and Chronic Application of Beta-Amyloid Fragment 25-35 in Cortical Cultures", Neuroscience Letters, 203(1): 61-65, 1996.
Chivers et al. "The CXXC Motif: A Rheostat in the Active Site", Biochemistry, 36(14): 4061-4066, 1997.
Choplin "Quantitative Drug Design", C.A. Ramsden, Chap. 17.2, p. 34-58, 1992.
Coppey et al. "Effect of Antioxidant Treatment of Streptozotocin-Induced Diabetic Rats on Endoneurial Blood Flow, Motor Nerve Conduction Velocity, and Vascular Reactivity of Epineurial Arterioles of the Sciatic Nerve", Diabetes, 50(8); 1927-937, 2001.
Crack et al. "Increased Infarct Size and Exacerbated Apoptosis in the Glutathione Peroxidase-1 (Gpx-1) Knockout Mouse Brain in Response to Ischemia/Reperfusion Injury", Journal of Neurochemistry, 78(6): 1389-1399, 2001.
Cui et al. "Neuronal NOS Inhibitor That Reduces Oxidative DNA Lesions and Neuronal Sensitivity Increases the Expression of Intact C-Fos Transcripts After Brain Injury", Journal of Biomedical Science, 8(4): 336-341, 2001.
D'Angio et al. "Oxygen Regulation of Gene Expression: A Study in Opposites", Molecular Genetic & Metabolism, 71: 371-380, 2000.
Dudek et al. "H(2)O(2)-Mediated Oxidative Stress Activates NF-Kappa B in Lens Epithelial Cells", Free Radical Biology & Medicine, 31(5): 651-658, 2001.
Espejo et al. "Differential Expression of Metallothioneins in the CNS of Mice With Experimental Autoimmune Encephalomyelitis", Neuroscience, 105(4): 1055-1065, 2001.
Fahn et al. "The Oxidant Stress Hypothesis in Parkinson's Disease: Evidence Supporting It", Annals in Neurology, 32(6): 804-812, 1992.
Fingl et al., "Goodman & Gilman's: The Pharmaceutical Basis of Therapeutics", McGraw-Hill Professional, Sec. I (Chap.1): 1-46, 2001.
Fleshner et al. "Dict, Androgens, Oxidative Stress and Prostate Cancer Susceptibility", Cancer Metastasis Reviews, 17(4): 325-330, 1998/99.
Foye "Principles of Medicinal Chemistry", Pharmaceutical Chemistry, 2nd Ed., p. 194-195, 1989.
Gan et al. "Purification and Properties of Thioltransferase", Journal of Biological Chemistry, 261(3): 996-1001, 1986.
Gockel et al. "Solution Behaviour and Zinc Complexation of Tripeptides With Cysteine and/or Histidine at Both Termini", Inorganica Chimica Acta, 272(1-2): 115-124, 1998.
Gong et al. "Human Hepatitis C Virus NS5A Protein Alters Intracellular Calcium Levels, Induces Oxidative Stress, and Activates STAT-3 and NF-Kappa B", Proc. Natl. Acad. Sci. USA, 98(17): 9599-9604, 2001.
Goto et al. "Magnetic Resonance Imaging Findings and Postoperative Neurologic Dysfunction in Eldery Patients Undergoing Coronary Artery Bypass Grafting", Annals of Thoracic Surgery, 72(1): 137-142, 2001.
Harding "Experimental Opacification of the Lens in Vivo and in Vitro", Sugar Cataract: Biochemistry, Epidemiology and Pharmacology, Chap.4: 125-217, 1991.
Jacobson "Reactive Oxygen Species and Programmed Cell Death", TIBS, 21: 83-86, 1996.
Jenner "Oxidative Damage in Neurodegenerative Disease", The Lancet, 344: 796-798, 1994.
Jones et al. "Dopamine-Induced Apoptosis Is Mediated by Oxidative Stress and Is Enhanced by Cyanide in Differentiated PC12 Cells", Journal of Neurochemistry, 74(6): 2296-2304, 2000.
Keles et al. "Effect of Corticosteroid Therapy on Serum and CSF Malondialdehyde and Antioxidant. Proteins in Multiple Sclerosis", Canadian Journal of Neurological Sciences, 28(2): 141-143, 2001.
Keller et al. "Mitochondrial Manganese Superoxide Dismutase Prevents Neural Apoptosis and Reduces Ischemic Brain Injury: Suppression of Peroxynitrite Production, Lipid Pcroxidation, and Mitochondrial Dysfunction", The Journal of Neuroscience, 18(2): 687-697, Jan. 15, 1998.
Khan et al. "S100 Protein: Its Use as a Marker of Cerebral Damage in Cardiac Operations", Annals of Thoracic Surgery, 72(2): 666-667, 2001.
Kim et al. "A Novel Dithiol Amide CB3 Attenuates Allergic Airway Disease Through Negative Regulation of P38 Mapk", American Journal of Respiratory and Critical Care Medicine, E-Published Ahead of Print, Apr. 22, 2010.
Kim et al. "The Cytosolic Antioxidant, Copper/Zinc Superoxide Dismutase, Attenuates Blood-Brain Barrier Disruption and Oxidative Cellular Injury After Photothrombotic Cortical Ischemia in Mice", Neuroscience, 105(4): 1007-1018, 2001.
Kosano et al. "Suppressive Effects of Thyroxine on Glucocorticoid (Gc)-Induced Metabolic Changes and Cataract Formation on Developing Chick Embryos", Experimental Eye Research, 72(6): 643-648, 2001.
Kowluru et al. "Abnormalities of Retinal Metabolism in Diabetes and Experimental Galactosemia. VII. Effect of Long-Telln Administration of Antioxidants on the Development of Retinopathy", Diabetes, 50(8): 1938-1942, 2001.
Lee et al. "HER2 Cytoplasmic Domain Generates Normal Mitogenic and Transforming Signals in a Chimeric Receptor", The EMBO Journal, 8(1): 167-173, 1989.
Lin et al. "The Involvement of a Stress-Activated Pathway in Equine Influenza Virus-Mediated Apoptosis", Virology, 287(1): 202-213, 2001.
Liu et al. "Heme Oxygenase-1 Plays an Important Protective Role in Experimental Autoimmune Encephalomyelitis", Neuroreport, 12(9): 1841-1845, 2001.
Liu et al. "Ischemic Injury and Faulty Gene Transcripts in the Brain", Trends in Neuroscience, 24(10): 581-588, 2001.
Lovell et al. "Decreased Thioredoxin and Increased Thioredoxin Reductase Levels in Alzheimer's Disease Brain", Free Radical Biology and Medicine, 28(3): 418-427, 2000.
Mann et al. "Glutathione S-Transferase Polymorphisms in MS: Their Relationship to Disability", Neurology, 54: 552-557, 2000.
Maulik et al. "Oxidative Stress Developed During Open Heart Surgery Induces Apoptosis: Reduction of Apoptotic Cell Death by Ebselen, A Glutathione Peroxidase Mimic", Journal of Cardiovascular Pharmacology, 36(5): 601-608, 2000.
Maytin et al. "Oxidant Stress in the Vasculature", Current Atherosclerosis Reports, 1(2): 156-164, 1999.
Nakamura et al. "Metabolic Coupling of Gutathione Between Mouse and Quail Cardiac Myocytes and Its Protective Role Against Oxidative Stress", Circulation Research, 74(5): 806-816, 1994. See Esp. 'Results and Discussion'.
Nunomura et al. "Neuronal RNA Oxidation in Alzheimer's Disease and Down's Syndrome", Annals of the NY Academy of Sciences, 893: 362-364, 1999.
Nunomura et al. "RNA Oxidation Is a Prominent Feature of Vulnerable Neurons in Alzheimer's Disease", Journal of Neuroscience, 19(6): 1959-1964, 1999.
Offen et al. "Prevention of Dopamine-Induced Cell Death by Thiol Antioxidants: Possible Implications for Treatment of Parkinson's Disease", Experimental Neurology, 141(1): 32-39, 1996.
Olanow "A Radical Hypothesis for Neurodegeneration", Trends in Neuroscience, TINS, 16(11): 439-444, 1993.
Olanow "Oxidation Reactions in Parkinson's Disease", Neurology, 40(Suppl. 3): 32-37, 1990.

Peiro et al. "High Glucose Induces Cell Death of Cultured Human Aortic Smooth Muscle Cells Through the Formation of Hydrogen Peroxide", British Journal of Pharmacology, 133(7): 967-974, 2001.

Penkowa et al. "Metallothionein Treatment Reduces Proinflammatory Cytokines IL-6 and TNF-Alpha and Apoptotic Cell Death During Experimental Autoimmune Encephalomyelitis (EAE)", Exp. Neurol., 170(1): 1-14, 2001.

Pettersen et al. "Long-Term Retention of a Novel Antioxidant Sulphur-Substituted Fatty Acid Analogue After Local Delivery in Porcine Coronary Arteries", Scandinavian Cardiovascular Journal, 35(2): 101-106, 2001.

Raina et al. "Genetic Evidence for Oxidaive Stress in Alzheimer's Disease", Neuroreport, 10(6): 1355-1357, 1999.

Reid et al. "The mRNA Level of the Potassium-Chloride Cotransporter KCC2 Covaries With Seizure Susceptibility in Inferior Colliculus of the Post-Ischemic Audiogenic Seizure-Prone Rat", Neuroscience Letters, 308(1): 29-32, 2001.

Rottkamp et al. "Oxidative Stress, Antioxidants, and Alzheimer Disease", Alzheimer Disease and Associated Disorders, 14(Suppl.1): S62-S66, 2000.

Saitoh et al. "Mammalian Thioredoxin Is a Direct Inhibitor of Apoptosis Signal-Regulating Kinase (ASK) 1", The EMBO Journal, 17(9): 2596-2606, 1998.

Schoonbroodt et al. "Oxidative Stress Interference With the Nuclear Factor-Kappa B Activation Pathways", Biochemical Pharmacology, 60(8): 1075-1083, 2000.

Shi et al. "Discovery of a Highly Selective and Efficient Reagent for Formation of Intramolecular Disulfide Bonds in Peptides", Journal of the American Chemical Society, 122(29): 6809-6815, 2000. p. 6810, Table 1.

Sinha et al. "Liposomal Antioxidants in Combating Ischemia-Reperfusion Injury in Rat Brain", Biomedical Pharmacotherapy, 55(5): 264-271, 2001.

The Parkinson Study Group "Effects of Tocopherol and Deprenyl on the Progression of Disability in Early Parkinson's Disease", New England Journal of Medicine, 328(3): 176-183, 1993.

Thomas et al. "Beta-Amyloid-Mediated Vasoactivity and Vascular Endothelial Damage", Nature, 380(6570): 168-171, 1996.

Tournier et al. "Requirement of JNK for Stress-Induced Activation of the Cytochrome C-Mediated Death Pathway", Science, 288(5467): 870-874, 2000.

Ueda et al. "Synthesis of New Oligopeptides and Their Scavenging Abilities Against Active Oxygen Species", Biochemistry and Molecular Biology International, 33(6): 1041-1048, 1994. See Esp. 'Results and Discussion'.

Voet et al. "Biochemistry", Wiley and Sons Inc., p. 382-383, 1990.

Wagberg et al. "N,N'-Diacetyl-L-Cystine (Dinac), the Disulphide Dimer of N-Acetylcysteine, Inhibits Atherosclerosis in WHHL Rabbits: Evidence for Immunomodulatory Agents as a New Approach to Prevent Atherosclerosis", Journal of Pharmacology and Experimental Thera py, 299(1): 76-82, 2001.

Watanabe et al. "Lipid Peroxidation Product 4-Hydroxy-2-Nonenal Acts Synergistically With Serotonin in Inducing Vascular Smooth Muscle Cell Proliferation", Atherosclerosis, 155(1): 37-44, 2001.

Yang et al. "Attenuation of Ischemia-Induced Mouse Brain Injury by SAG, A Redox-Inducible Antioxidant Protein", Journal of Cerebral Blood Flow and Metabolism, 21(6): 722-733, 2001.

* cited by examiner

Protection from Reactive Oxygen Species (ROS) by CB and NOXi

```
                        SEQUENCE LISTING

<160> NUMBER OF SEQ ID NOS: 21

<210> SEQ ID NO 1
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 1

Cys Gly Pro Cys
1

<210> SEQ ID NO 2
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N terminal hydrophobic or non-charged moiety
<220> FEATURE:
<221> NAME/KEY: misc_feature
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: C terminal hydrophobic or non-charged moiety
```

```
<400> SEQUENCE: 2

Cys Xaa Xaa Cys
1

<210> SEQ ID NO 3
<211> LENGTH: 1
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N terminal hydrophobic or non-charged moiety

<400> SEQUENCE: 3

Cys
1

<210> SEQ ID NO 4
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N terminal hydrophobic or non-charged moiety
<220> FEATURE:
<221> NAME/KEY: misc_feature
<222> LOCATION: (2)..(2)
<223> OTHER INFORMATION: Any amino acid

<400> SEQUENCE: 4

Cys Xaa
1

<210> SEQ ID NO 5
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N terminal hydrophobic or non-charged moiety
<220> FEATURE:
<221> NAME/KEY: misc_feature
<222> LOCATION: (2)..(3)
<223> OTHER INFORMATION: Ant amino acid

<400> SEQUENCE: 5

Cys Xaa Xaa
1

<210> SEQ ID NO 6
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N terminal hydrophobic or non-charged moiety
<220> FEATURE:
<221> NAME/KEY: misc_feature
<222> LOCATION: (2)..(3)
<223> OTHER INFORMATION: Any amino acid
```

```
<400> SEQUENCE: 6

Cys Xaa Xaa Cys
1

<210> SEQ ID NO 7
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Any amino acid
<220> FEATURE:
<221> NAME/KEY: MOD_RES
<222> LOCATION: (4)..(4)
<223> OTHER INFORMATION: C terminal hydrophobic or non-charged moiety

<400> SEQUENCE: 7

Cys Xaa Xaa Cys
1

<210> SEQ ID NO 8
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Any amino acid
<220> FEATURE:
<221> NAME/KEY: MOD_RES
<222> LOCATION: (3)..(3)
<223> OTHER INFORMATION: C terminal hydrophobic or non-charged moiety

<400> SEQUENCE: 8

Xaa Xaa Cys
1

<210> SEQ ID NO 9
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: C terminal hydrophobic or non-charged moiety

<400> SEQUENCE: 9

Xaa Cys
1

<210> SEQ ID NO 10
<211> LENGTH: 1
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: C terminal hydrophobic or non-charged moiety
```

```
<400> SEQUENCE: 10

Cys
1

<210> SEQ ID NO 11
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Any amino acid

<400> SEQUENCE: 11

Cys Xaa Xaa Cys
1

<210> SEQ ID NO 12
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Any amino acid

<400> SEQUENCE: 12

Cys Xaa Xaa
1

<210> SEQ ID NO 13
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Any amino acid

<400> SEQUENCE: 13

Cys Xaa
1

<210> SEQ ID NO 14
<211> LENGTH: 1
<212> TYPE: PRT
<213> ORGANISM: Artificial sequence
<220> FEATURE:
<223> OTHER INFORMATION: Synthetic peptide

<400> SEQUENCE: 14

Cys
1

<210> SEQ ID NO 15
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(2)
<223> OTHER INFORMATION: Any amino acid
```

-continued

```
<400> SEQUENCE: 15

Xaa Xaa Cys
1

<210> SEQ ID NO 16
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Any amino acid

<400> SEQUENCE: 16

Xaa Cys
1

<210> SEQ ID NO 17
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N terminal hydrophobic or non-charged moiety
<220> FEATURE:
<221> NAME/KEY: misc_feature
<222> LOCATION: (2)..(2)
<223> OTHER INFORMATION: Any amino acid
<220> FEATURE:
<221> NAME/KEY: MOD_RES
<222> LOCATION: (3)..(3)
<223> OTHER INFORMATION: C terminal hydrophobic or non-charged moiety

<400> SEQUENCE: 17

Cys Xaa Cys
1

<210> SEQ ID NO 18
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N terminal hydrophobic or non-charged moiety
<220> FEATURE:
<221> NAME/KEY: misc_feature
<222> LOCATION: (2)..(2)
<223> OTHER INFORMATION: Any amino acid

<400> SEQUENCE: 18

Cys Xaa Cys
1

<210> SEQ ID NO 19
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Any amino acid
```

```
<220> FEATURE:
<221> NAME/KEY: MOD_RES
<222> LOCATION: (3)..(3)
<223> OTHER INFORMATION: C terminal hydrophobic or non-charged moiety

<400> SEQUENCE: 19

Cys Xaa Cys
1

<210> SEQ ID NO 20
<211> LENGTH: 3
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Any amino acid

<400> SEQUENCE: 20

Cys Xaa Cys
1

<210> SEQ ID NO 21
<211> LENGTH: 2
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Any amino acid

<400> SEQUENCE: 21

Xaa Cys
1
```

MULTI-COMPONENT ANTIOXIDANT COMPOUNDS, PHARMACEUTICAL COMPOSITIONS CONTAINING SAME AND THEIR USE FOR REDUCING OR PREVENTING OXIDATIVE STRESS

RELATED APPLICATIONS

This application is a continuation of U.S. patent application Ser. No. 13/086,429 filed on Apr. 14, 2011, which is a continuation of U.S. patent application Ser. No. 11/797,590 filed on May 4, 2007, now abandoned, which is a continuation of U.S. patent application Ser. No. 10/234,319 filed on Sep. 5, 2002, now abandoned, which is a National Phase of PCT Patent Application No. PCT/IL01/00984 having an International Filing Date of Oct. 25, 2001, which claims the benefit of priority of United Kingdom Patent Application No. 0026254.3 filed on Oct. 26, 2000, now Patent No. GB2368339. The contents of all of the above applications are incorporated by reference as if fully set forth herein.

FIELD AND BACKGROUND OF THE INVENTION

The present invention relates to antioxidant compounds, pharmaceutical compositions containing same and their use for preventing or reducing oxidative stress. More particularly, the present invention relates to novel non-central nervous system (CNS) and CNS targeted antioxidants and their use in treating non-CNS and CNS disorders, diseases or conditions associated with a formation of oxidative stress.

Oxidative Stress:

The cellular physiological reduction-oxidation (redox) state, which is dependent on concentrations of oxygen and reactive oxygen species (ROS), is involved in controlling central biochemical regulatory processes, such as tyrosine phosphorylation, regulation of transcription and alteration in messenger RNA stability (1) and it is finely balanced by specific enzymes, such as superoxide dismutase (SOD), catalase, gluthatione peroxidase and thioredoxin, and selective antioxidants, such as glutathione. Regulated homeostasis of the intracellular redox state is essential to the proper physiological functioning of the cell, however, overproduction of (ROS), at levels exceeding the neutralization capacity of cellular antioxidant defenses, generates an oxidative state, termed oxidative stress. Such oxidative stress can lead to oxidative injury via processes such as inflammation, apoptosis and mutagenesis.

Inflammation, a normal physiological process involving limited tissue injury, can be pathogenic if uncontrolled, as under conditions of excessive oxidative stress. In such cases, elevation of ROS, via alterations in expression of redox state-responsive genes, causes the ubiquination and destruction of the NF-κB inhibitory proteins, thereby allowing NF-κB to bind to target gene promoters, a pivotal event in the upregulation of multiple pro-inflammatory cytokines (2). An excess of free radicals has been identified in many diseases associated with inflammation, such as sepsis, multiple sclerosis (MS), stroke, myocarditis and rheumatoid arthritis.

While the development and maintenance of a healthy tissue involves properly regulated apoptosis, interference with this process contributes to various pathologies including tumor promotion, immunodeficiency diseases and neurodegenerative disorders. It has been shown that elevation of the intracellular oxidative state, either via addition of reactive oxygen species (ROS) or depletion of cellular antioxidants, can cause apoptosis (3, 4) and much evidence has accumulated linking oxidative stress to activation of specific enzymes involved in apoptosis.

One such enzyme, essential in the signaling pathway of cytochrome c mediated apoptosis, is c-Jun N-terminal kinase (JNK) which is activated in response to UV radiation, cis-platinum treatment or cellular stress. It has been demonstrated that disruption of JNK protects against UV induced apoptosis, resulting in impairment of the mitochondrial death signaling pathway (5).

In a previous study (6), ROS were shown to play a role as intermediate factors in the pathway of various signal transduction pathways involving thioredoxin, a ubiquitous enzyme in all living cells containing a specific redox-active site. Thioredoxin acts as an inhibitor of oxidative stress induced apoptosis by binding to, and thereby inhibiting, apoptosis signal regulating kinase-1 (ASK1), a protein mediating oxidative stress-induced apoptosis via a redox state responsive domain. However, under conditions of excessive oxidative stress, oxidized thioredoxin dissociates from ASK1, thereby activating it and triggering apoptosis.

Pathologies Associated with Oxidative Stress:

Oxidant injury has been implicated in the pathology of a wide-ranging variety of diseases, including many of major clinical and economic impact, such as cardiovascular, neurological, metabolic, infectious, hepatic, pancreatic, rheumatoid, malignant and immunological diseases, as well as conditions such as sepsis, cataract, amyotrophic lateral sclerosis and congenital diseases such as Down syndrome, multiple organ dysfunction (7) and cystic fibrosis Described below are some of the most widespread and devastating diseases in which oxidative stress is an etiological factor.

Neurodegenerative Pathologies-Involvement of Inflammation and Oxidative Stress: Evidence has accumulated demonstrating a strong linkage of oxidative stress with pathogenesis of major human neurodegenerative disorders (8-10) including Parkinson's disease (11, 12), Alzheimer's disease (13-15), Creutzfeldt-Jakob disease (16) as well as MS (17).

The different pathological markers characteristic of various neurodegenerative diseases, such as Lewy bodies in Parkinson's disease and amyloid plaques in Alzheimer's disease, indicate different causal factors in the initiation of these diseases. However, there is growing evidence that, once initiated, the progression of a large number of neurodegenerative diseases follows similar cellular pathways. Namely, elevation of the intracellular oxidative state in specific regions of the CNS appears to be an important factor in the etiology of diseases such as Alzheimer's disease, Parkinson's disease, spongiform encephalopathies, degenerative diseases of the basal ganglia, motoneuron diseases and memory loss.

For example, a role for oxidative stress in the pathogenesis of Alzheimer's disease was indicated in a recent analysis of the relationship between β-amyloid protein fragment and oxygen radical formation. This study employed a highly sensitive system, utilizing monitoring blood vessel vasoactive responses, in which β-amyloid-mediated enhancement of phenylephrine-mediated vasoconstriction could be abrogated by pretreatment of blood vessels with SOD, an enzyme which scavenges oxygen free radicals (15). Other studies have shown that oxidative stress and free radical production are linked to the presence of β-amyloid fragment (amino acids 25-35) and likely contribute to neurodegenerative events associated with Alzheimer's disease (18). Further studies have shown extensive RNA oxidation in neurons in Alzheimer's disease and Down's syndrome (13, 14) and genetic evidence for oxidative stress in Alzheimer's disease has also been reported (19, 20).

Evidence of a role for elevated oxidative stress in pathogenesis of MS was provided in studies analyzing the role of metallothioneins, enzymes involved in maintenance of redox homeostasis, in MS or experimental autoimmune encephalomyelitis (EAE) (21, 22), in studies demonstrating increased lipid peroxidation in serum and cerebrospinal fluid of MS patients and in studies demonstrating the role of heme oxygenase-1 (HO-1), a heat shock protein induced by oxidative stress, in the progression of EAE (23).

In the case of scrapies, a type of spongiform encephalopathy occurring in sheep, it was demonstrated that pathogenesis is mediated via microglia cells which respond to prion protein fragment Prp$^{106-126}$ by increasing oxygen radical production (16).

Diabetes: There is convincing experimental and clinical evidence that the generation of ROS is increased in both types of diabetes and that the onset of diabetes is closely associated with oxidative stress. Recently, it was demonstrated that intracellular content of the oxidant $H_2O_2$, visualized with 2',7'-dichlorofluorescein and quantified by flow cytometry, is increased following treatment with high glucose levels. Concomitant elevation of lactate dehydrogenase activity was detected suggesting that high glucose promotes necrotic cell death through $H_2O_2$ formation, which may contribute to the development of diabetic vasculopathy (24). Consistent with these results, a recent study has demonstrated that long-term administration of antioxidants can inhibit the development of the early stages of diabetic retinopathy (25). Other studies carried out with treatment of diabetic rats with antioxidants suggest that diabetes-induced oxidative stress and the generation of superoxide may be partially responsible for the development of diabetic vascular and neural complications (26).

Cataract Formation: A role for oxidant injury in cataract formation was shown in early studies demonstrating that decreased levels of the antioxidant hepatic glutathione-S-transferase (GSH) are associated with increasing opacity of the lens (27). Later studies have shown that in the mammalian lens, intracellular oxidants produced by light induced oxidative processes cause oxidative damage, result in changes in gene expression, and are causally related to cataract formation. It is presently believed that $H_2O_2$ is the major oxidant to which the lens is exposed (28).

Infectious Diseases: Harmful levels of oxygen free radicals and nitric oxide (NO) are generated in a diverse range of, and are essential to, the pathogenesis of many types of microbial infections (29). Viral diseases whose pathogenesis is associated with oxidative stress include hepatitis C, AIDS, influenza and diseases caused by various neurotropic agents. In many kinds of viral infections high levels of NO generate highly reactive nitrogen oxide species including reactive oxygen intermediates as well as peroxynitrite, via interaction with oxygen radicals. These species of reactive nitrogen cause oxidant injury as well as mutagenesis via oxidation of various biomolecules. Recent evidence has also demonstrated that oxidative stress induced by NO causes further harm by increasing viral mutation rates and by suppressing type 1 helper T cell function. For example, studies employing the equine influenza virus (EIV) influenza model have shown that viral infection causes cytopathogenic effects and apoptosis as a result of oxidative stress (30). Another study has shown that progression of human hepatitis C virus infection involves triggering of oxidative stress via a mechanism in which the non-structural HCV protein NS5A triggers elevation of ROS in mitochondria, leading to the nuclear translocation and constitutive activation of the pro-inflammatory transcription factors NF-κB and STAT-3 (31).

Neurological Dysfunction Following Cardiac Surgery: Cardiac operations, such as coronary bypass surgery, following multiple infarctions has been shown to significantly increase the risk of neurologic dysfunction, such as impairment of brain function and memory (32-34). Studies have provided evidence that such neurological impairment is associated with oxidative stress (35).

Cardiovascular Diseases: The pathogenesis of major cardiovascular diseases, such as atherosclerosis, hypertension, stroke and restenosis, has been shown to involve oxidative stress. Such oxidant stress in the vasculature causes adverse vessel reactivity, vascular smooth muscle cell proliferation, macrophage adhesion, platelet activation, and lipid peroxidation (36). In the case of atherosclerosis, one of the leading causes of mortality in the developed world, pathogenesis specifically involves inflammation and oxidation of lipoprotein-derived lipids (37).

Recent studies have shown that cerebral ischemia followed by reperfusion leads to elevated oxidative stress (38, 39) and that such oxidative stress can cause damage to genes in brain tissue despite functional DNA repair mechanisms (40). Involvement of such oxidative stress in ischemia-associated pathogenesis was further demonstrated in studies reporting increased infarct size and exacerbated apoptosis in glutathione peroxidase-1 (Gpx-1) knockout mouse brain subjected to ischemia/reperfusion injury (41).

Cancer: Studies have shown that oxidative stress is involved in development of cancers, such as prostate cancer, the most common human malignancy and the second leading cause of cancer deaths among men in Western nations (42).

Thus, the pathogenesis of a very broad variety of diseases involves oxidative stress and, as such, methods of reducing oxidative state may provide an attractive means of treating such diseases.

Prior Art Methods of Treating Disease Via Reduction of Oxidative Stress:

Various prior art methods of treating diseases associated with oxidative stress via reduction of oxidative stress have been attempted and have demonstrated the potential effectiveness of treating disease by restoring redox balance. These have involved either prevention of enzymatic production of ROS by specific inhibitors or introduction of exogenous antioxidants for restoring redox balance.

Diseases of the CNS: To overcome high oxidative stress for the treatment of diseases of the CNS, it is desirable to administer agents capable of reducing oxidative stress into the CNS. However, the CNS is physiologically separated from the rest of the body and from the peripheral blood circulation, by the blood brain barrier (BBB). Since the BBB constitutes a very effective barrier for the passage of agents, such as antioxidants, lacking a selective transporter, such as enzymes or other proteins capable of decreasing oxidative stress, administration of such agents must be via direct injection into the brain or cerebrospinal fluid (CSF). Such a route of administration, however, is unacceptably risky, cumbersome and invasive and thus represents a major drawback for this treatment modality.

One approach has employed administration of the antioxidants vitamin E and vitamin C for treatment of neurological diseases, such as Parkinson's disease (43, 44). Vitamin E was found to be ineffective at decreasing oxidative stress in the substantia nigra and, although capable of crossing the BBB, is trapped in the cell membrane and therefore does not reach the cytoplasm where its antioxidant properties are needed. Vitamin C was shown to cross the BBB to some extent, via a selective transporter, nevertheless it has also been shown to be ineffective in treating neurodegenerative diseases of the CNS.

In another approach, antioxidant compounds characterized by a combination of low molecular weight and membrane miscibility properties for permitting the compounds to cross the BBB of an organism, a readily oxydizable (i.e., reducing) chemical group for exerting antioxidation properties and a chemical make-up for permitting the compounds or their intracellular derivative to accumulate within the cytoplasm of cells, have been employed to treat pathology, including CNS pathology, associated with oxidative stress (44).

Diseases of Non-CNS Tissues:

Systemic Administration of Antioxidants: The major prior art approach used for reducing oxidative stress in non-CNS tissues has employed administration antioxidants.

The antioxidant NAC has been employed to treat canine kidney cells so as to attenuate EIV-induced cytopathic effect and apoptosis (30) and to treat atherosclerosis and restenosis following angioplasty (46). Dimers of NAC have also been employed for treating atherosclerosis (37).

The sulphur-containing fatty acid with antioxidant properties, tetradecylthioacetic acid, has been employed to achieve long-term reduction of restenosis following balloon angioplasty in porcine coronary arteries (47).

The antioxidants pyrrolidine dithiocarbamate (PDTC) and NAC have been used to prevent pathogenic HCV mediated constitutive activation of the pro-inflammatory transcription factor STAT-3 (31).

Synthetic antioxidants have also been employed to treat oxidative stress related disease. For example, treatment of asthma has been attempted by reducing the levels of free oxygen using the synthetic reactive oxygen inhibitor 2,4-diaminopyrrolo-2,3-dipyrimidine (48).

Apoptosis in an ischemic swine heart model has been treated with ebselen, a glutathione peroxidase mimic (35).

The cytosolic antioxidant, copper/zinc superoxide dismutase, has been employed to treat blood-brain barrier disruption and infarction following cerebral ischemia-reperfusion (49). Attenuation of ischemia-induced mouse brain injury has been attempted by administration of SAG, a redox-inducible antioxidant protein (50).

Administration of Metabolic Regulators of Antioxidants: Another approach has attempted to employ metabolic regulators of antioxidants to reduce oxidative stress.

One study has attempted prevention of cataract in a chick embryo model via administration of thyroxine to drive metabolic maintenance of hepatic GSH levels so as to reduce oxidative stress induced by glucocorticoids (51)

Hemin, an inducer of the oxidative stress induced protein, heme oxygenase-1, has been utilized to inhibit progression of EAE (23).

Administration of corticosteroids has been employed to treat lipid peroxidation in MS patients (24).

Stimulation of production of the endogenous antioxidant reduced glutathione has been attempted for treating acute respiratory distress syndrome (ARDS), a condition characterized by overproduction of oxidants or ROS by the immune system, by administration of the drug pro-cysteine (Free Radical Sciences Inc., CA, U.S.). This drug functions by boosting cellular production of glutathione by upregulation of cellular cysteine uptake.

A common feature characterizing all of the above described and other antioxidant compounds is their limited diversity in structure, body distribution, cellular distribution, organelle distribution, and/or antioxidant properties, etc. As such, any given antioxidant may prove useful for some applications, yet less or non-useful for other applications. In some cases, a specific antioxidant may efficiently reduce oxidative stress in some body parts, some cells, or some subcellular structures, yet not in others.

There is thus, a great need for, and it would be highly advantageous to have, an antioxidant compound which is devoid of the above limitations, which compound will by hydrolyzed in vivo to a plurality of different antioxidant species which will act in concert to reduce or prevent oxidative stress in a plurality of tissues, cell types and cellular organelles, so as to combat disease, syndromes and conditions associated with formation of oxidative stress, both in non-CNS and CNS tissues.

SUMMARY OF THE INVENTION

According to one aspect of the present invention there is provided an antioxidant compound comprising (a) a peptide including at least three amino acid residues of which at least two being cysteine residues, each having a readily oxidizable sulfhydryl group for effecting antioxidation; and at least two peptide bonds each being cleavable by at least one intracellular peptidase; and (b) a first hydrophobic or non-charged moiety being attached to an amino terminal of the peptide via a first bond and a second hydrophobic or non-charged moiety being attached to a carboxy terminal of the peptide via a second bond, the first hydrophobic or non-charged moiety and the second hydrophobic or non-charged moiety are selected so as to provide the antioxidant compound with membrane miscibility properties for permitting the antioxidant compound to cross cellular membranes; wherein cleavage of the at least two peptide bonds by the at least one intracellular peptidase results in generation of a plurality of antioxidant species, each including at least one of the cysteine residue having the readily oxidizable sulfhydryl group and which is also active in effecting antioxidation, thereby providing for a plurality of different antioxidant species acting in synergy in exerting antioxidation.

According to another aspect of the present invention there is provided a pharmaceutical composition for preventing or reducing oxidative stress, the composition comprising a pharmaceutically acceptable carrier and, as an active ingredient, an effective amount of an antioxidant compound, the antioxidant compound including: (a) a peptide including at least three amino acid residues of which at least two being a cysteine residues, each having a readily oxidizable sulfhydryl group for effecting antioxidation; and at least two peptide bond each being cleavable by at least one intracellular peptidase; and (b) a first hydrophobic or non-charged moiety being attached to an amino terminal of the peptide via a first bond and a second hydrophobic or non-charged moiety being attached to a carboxy terminal of the peptide via a second bond, the first hydrophobic or non-charged moiety and the second hydrophobic or non-charged moiety are selected so as to provide the antioxidant compound with membrane miscibility properties for permitting the antioxidant compound to cross cellular membranes; wherein cleavage of the at least two peptide bonds by the at least one intracellular peptidase results in generation of a plurality of antioxidant species each including at least one of the cysteine residue having the readily oxidizable sulfhydryl group and which is also active in effecting antioxidation, thereby providing for a plurality of different antioxidant species acting in synergy in exerting antioxidation.

According to further features in preferred embodiments of the invention described below, the antioxidant compound has a general formula of:

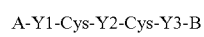

wherein, Cys is a cysteine residue, A is the first hydrophobic or non-charged moiety; B is the second hydrophobic or non-charged moiety; Y1, Y2 and Y3 are each individually one or more amino acid residues in the range of 0-30 residues, with the provision that Y1, Y2 and Y3 collectively provide for at least two amino acid residues in the peptide.

According to still further features in the described preferred embodiments the A is selected from the group consisting of N-acetyl, tert butyl, isopropyl, n-butyl and n-pentyl.

According to still further features in the described preferred embodiments the B is selected from the group consisting of amide and ester.

According to still further features in the described preferred embodiments cleavage of the first bond and/or the second bond by a cellular hydrolase results in loosing the membrane miscibility.

According to still further features in the described preferred embodiments the cleavage of the first bond and/or the second bond by a cellular hydrolase results in formation of additional antioxidant species acting in synergy.

According to still further features in the described preferred embodiments the first bond and the second bond are each independently an ester or peptide bond.

According to still further features in the described preferred embodiments each of the first hydrophobic or non-charged moiety and the second hydrophobic or non-charged moiety is selected from the group consisting of alkyl, aryl, alkene, arene and cholesteril having a backbone of 2-50 carbon atoms.

According to still further features in the described preferred embodiments the first hydrophobic or non-charged moiety and the second hydrophobic or non-charged moiety are selected so as to enable the antioxidant compound to cross a blood barrier.

According to still further features in the described preferred embodiments the blood barrier is selected from the group consisting of a blood brain barrier, a blood retinal barrier and a blood testis barrier.

According to yet another aspect of the present invention there is provided a method of treating a disease associated with formation of oxidative stress in a subject, the method comprising locally or systemically administering to the subject an antioxidant compound comprising: (a) a peptide including at least three amino acid residues of which at least two being cysteine residues each having a readily oxidizable sulfhydryl group for effecting antioxidation; and at least two peptide bonds each being cleavable by at least one intracellular peptidase; and (b) a first hydrophobic or non-charged moiety being attached to an amino terminal of the peptide via a first bond and a second hydrophobic or non-charged moiety being attached to a carboxy terminal of the peptide via a second bond, the first hydrophobic or non-charged moiety and the second hydrophobic or non-charged moiety are selected so as to provide the antioxidant compound with membrane miscibility properties for permitting the antioxidant compound to cross cellular membranes; wherein cleavage of the at least two peptide bonds by the at least one intracellular peptidase results in generation of several antioxidant species each including at least one of the cysteine residues having the readily oxidizable sulfhydryl group and which is also active in effecting antioxidation, thereby providing for a plurality of different antioxidant species acting in synergy in exerting antioxidation.

According to further features in preferred embodiments of the invention described below, the disease associated with formation of oxidative stress is a central nervous system disease.

According to still further features in the described preferred embodiments, the central nervous system disease is selected from the group comprising a neurodegenerative disorder, Parkinson's disease, Alzheimer's disease, Creutzfeldt-Jakob disease, cerebral ischemia, multiple sclerosis, a degenerative disease of the basal ganglia, a motoneuron disease, scrapies, spongiform encephalopathy, a neurological viral disease, a motoneuron disease, post-surgical neurological dysfunction, memory loss and memory impairment.

According to still further features in the described preferred embodiments, the disease associated with formation of oxidative stress is a non-central nervous system disease. According to still further features in the described preferred embodiments, the non-central nervous system disease is selected from the group comprising rheumatoid arthritis, cataract, Down syndrome, cystic fibrosis, diabetes, acute respiratory distress syndrome, asthma, post-surgical neurological dysfunction, amyotrophic lateral sclerosis, atherosclerotic cardiovascular disease, hypertension, post-operative restenosis, pathogenic vascular smooth muscle cell proliferation, pathogenic intra-vascular macrophage adhesion, pathogenic platelet activation, pathogenic lipid peroxidation, myocarditis, stroke, multiple organ dysfunction, complication resulting from inflammatory processes, AIDS, cancer, aging, bacterial infection, sepsis; viral disease, AIDS, hepatitis C, influenza and a neurological viral disease.

According to still another aspect of the present invention there is provided a method of treating a habit associated with formation of oxidative stress in a subject, the method comprising locally or systemically administering to the subject an antioxidant compound comprising: (a) a peptide including at least three amino acid residues of which at least two being cysteine residues each having a readily oxidizable sulfhydryl group for effecting antioxidation; and at least two peptide bonds each being cleavable by at least one intracellular peptidase; and (b) a first hydrophobic or non-charged moiety being attached to an amino terminal of the peptide via a first bond and a second hydrophobic or non-charged moiety being attached to a carboxy terminal of the peptide via a second bond, the first hydrophobic or non-charged moiety and the second hydrophobic or non-charged moiety are selected so as to provide the antioxidant compound with membrane miscibility properties for permitting the antioxidant compound to cross cellular membranes; wherein cleavage of the at least two peptide bonds by the at least one intracellular peptidase results in generation of several antioxidant species each including at least one of the cysteine residues having the readily oxidizable sulfhydryl group and which is also active in effecting antioxidation, thereby providing for a plurality of different antioxidant species acting in synergy in exerting antioxidation.

According to further features in preferred embodiments of the invention described below, the habit associated with formation of oxidative stress is selected from the group comprising aging, smoking, sun tanning, cancer treatment, radiation, cocaine consumption and morphine consumption.

According to still further features in the described preferred embodiments, the antioxidant compound is administered in a pharmaceutical composition which includes a pharmaceutically acceptable carrier.

According to still further features in the described preferred embodiments, the pharmaceutically acceptable carrier adapts the composition for administration by a route selected from the intranasal, transdermal, intradermal, oral, buccal, parenteral, topical, rectal and inhalation route.

According to still further features in the described preferred embodiments, the carrier provides the antioxidant compound in solution, suspension, emulsion, gel or skin pad.

According to still further features in the described preferred embodiments, the composition further includes a formulating agent selected from the group consisting of a suspending agent, a stabilizing agent and a dispersing agent.

The present invention successfully addresses the shortcomings of the presently known configurations by providing novel multifunctional antioxidant compounds which are non-central nervous system and central nervous system targeted antioxidants, N- and/or C-terminal blocked peptide derivatives for the use in treatment of non-central nervous system and central nervous system disorders related to oxidation processes.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
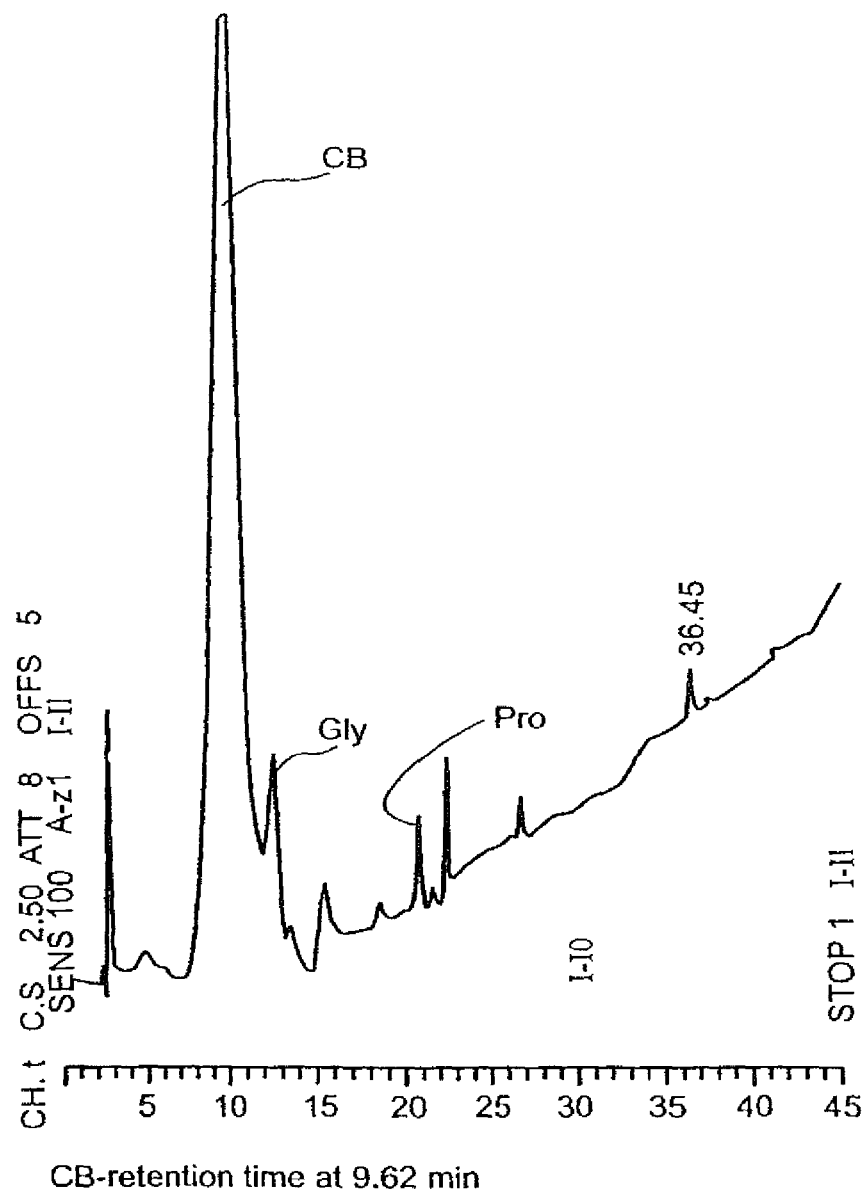
FIG. 1 shows the HPLC profile of purified N-acetyl cysteine-glycine-proline-cysteine-amid (referred to herein as CB, SEQ ID NO:1)) compound according to the present invention.

The present invention is of novel non-CNS and CNS targeted antioxidant compounds effective in treating non-CNS and CNS disorders, diseases or conditions associated with the formation of oxidative stress. More specifically, the compounds of the present invention can be used for the treatment of neurodegenerative disorders in which the pathology in the CNS is associated with oxidative stress, and for treatment of non-CNS tissues in conditions associated with overproduction of oxidants. Moreover, the novel compounds of the present invention can also be used for improving cognitive skills such as memory.

Before explaining at least one embodiment of the invention in detail, it is to be understood that the invention is not limited in its application to the details set forth in the following description or illustrated in the examples. The invention is capable of other embodiments or of being practiced or carried out in various ways. Also, it is to be understood that the phraseology and terminology employed herein is for the purpose of description and should not be regarded as limiting.

The principles of operation of the compounds according to the present invention may be better understood with reference to the examples and accompanying descriptions.

Antioxidant compounds are used according to the present invention to relieve oxidative stress within cells. A compound which can be used to relieve oxidative stress according to the present invention (i) has a combination of molecular weight and membrane miscibility properties rendering it capable of crossing blood barriers; (ii) includes a readily oxidizable (i.e., reduced) chemical group, such as, but not limited to, a sulfhydryl (—SH) group derived from a cysteine amino acid residue, for exerting its antioxidation properties; and (iii) has a chemical make-up for permitting it or its cellular derivative(s) to accumulate within the cytoplasm of cells. Collectively, these properties render the compounds of the present invention suitable for treatment of neurodegenerative disorder of the central nervous system, as well as for treating conditions in which non-CNS tissues, such as, but not limited to, the lungs and/or heart, are damaged due to overproduction of oxidants (i.e., reactive oxygen species), which is the case in, for example, acute respiratory distress syndrome, amyotrophic lateral sclerosis, atherosclerotic cardiovascular disease, multiple organ dysfunction, complication resulting from inflammatory processes, AIDS, cancer and aging.

As used in the specifications herein, "non-CNS" tissues refers to all body tissues, such as peripheral central nervous system tissues and non-nervous system tissues, with the exclusion of CNS tissues such as the brain and spinal cord.

As is further detailed in the background section above, prior art antioxidant compounds are limited in their structure diversity, body distribution, cellular distribution, organelle distribution, and/or antioxidant properties and capabilities, etc. As such, prior art antioxidant compounds are useful for some applications, yet less or non-useful for other applications.

To overcome the limitations inherent to prior art antioxidant compounds and their use, the present invention teaches novel compounds which are hydrolyzed in vivo to a plurality of different antioxidant species, which act in concert to reduce or prevent oxidative stress in a plurality of tissues, cell types and cellular organelles, so as to combat disease, syndromes and conditions associated with formation of oxidative stress both in the body periphery and in the brain.

Thus, according to one aspect of the present invention there is provided an antioxidant compound which includes a peptide including at least three amino acid residues of which at least two are cysteine residues, each having a readily oxidizable sulfhydryl group which serves for effecting antioxidation. The peptide, which is an antioxidant in itself, also includes at least two peptide bonds each is cleavable by at least one intracellular peptidase. The antioxidant compound of the present invention further includes a first hydrophobic or non-charged moiety which is attached to an amino terminal of the peptide via a first bond and a second hydrophobic or non-charged moiety which is attached to a carboxy terminal of the peptide via a second bond. The first and second hydrophobic or non-charged moieties are selected so as to provide the antioxidant compound with membrane miscibility properties, for permitting the antioxidant compound to cross cellular membranes. The antioxidant compounds of the present invention are characterized by the following unique and advantageous feature. Cleavage of the peptide bonds of the peptide by the intracellular peptidase(s) results in generation of a plurality of antioxidant species, each including at least one of the cysteine residues having the readily oxidizable sulfhydryl group and which is also active in effecting antioxidation, thereby providing a plurality of different antioxidant species acting in synergy in exerting antioxidation.

Thus, the antioxidant compound of the present invention is a peptide prodrug which penetrates the cells due to its solubility in the cell membrane. Upon entering the cytoplasm of a cell, the prodrug is cleaved by one or several intracellular peptidases, to release a plurality of different antioxidant species, each having at least one readily oxidizable sulfhydryl group to exert the antioxidative properties and acting in synergy in exerting antioxidation. Each cleaved species acts according to its biological half-life and independently of the other generated species to exert antioxidation. It will be appreciated in this respect that different cells consist of a selective set of different peptidases/esterases.

As used herein in the specification, the term "prodrug" refers to an agent which is converted into an active parent drug in vivo. Prodrugs are often useful because in some instances they may be easier to administer than the parent drug itself. They may, for instance, be bioavailable by oral administration whereas the parent drug is not. The prodrug may also have improved solubility compared to the parent drug in pharmaceutical compositions.

As used herein in the specification and in the claims section below the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body, or less immunogenic. Such modifications include, but are not limited to, cyclization, N-terminus modification, C-terminus modification, peptide bond modification, including, but not limited to, $CH_2$—NH, $CH_2$—S, $CH_2$—S=O, O=C—NH, $CH_2$—O, $CH_2$—$CH_2$, S=C—NH, CH=CH or CF=CH, backbone modification and residue modification. Methods for preparing peptidomimetic compounds are well known in the art and are specified, for example, in (53), which is incorporated by reference as if fully set forth herein. Further detail in this respect are provided hereinunder.

Thus, a peptide according to the present invention can be a cyclic peptide. Cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds).

Cyclization via formation of S—S bonds through incorporation of two Cys residues, in addition to the Cys residues exerting antioxidation, is also possible. Additional side-chain to side chain cyclization can be obtained via formation of an interaction bond of the formula —(—$CH_2$—)$_n$—S—$CH_2$—C—, wherein n=1 or 2, which is possible, for example, through incorporation of Cys or homoCys and reaction of its free SH group with, e.g., bromoacetylated Lys, Orn, Dab or Dap.

Peptide bonds (—CO—NH—) within the peptide may be substituted, for example, by N-methylated bonds (—N(CH$_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH=CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2 to 3) at the same time.

Natural aromatic amino acids, Trp, Tyr and Phe, may be substituted for synthetic non-natural acid such as TIC, naphthyl (Nol), ring-methylated derivatives of Phe, halogenated derivatives of Phe or o-methyl-Tyr.

Accordingly, as used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids which are linked via a peptide bond or a peptide bond analog to at least one addition amino acid as this term is defined herein.

An amino acid residue is understood to be an amino acid as this term is defined herein when serving as a building block or unit in a peptide, as this term is defined herein.

Tables 1-2 below list all the naturally occurring amino acids (Table 1) and non-conventional or modified amino acids (Table 2).

TABLE 1

Naturally occurring amino acids.

| Amino acid | Three-letter abbreviation | One-letter symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any amino acid as above | Xaa | X |

TABLE 2

Non-conventional or modified amino acids.

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |

TABLE 2-continued

Non-conventional or modified amino acids.

| Non-conventional amino acid | Code | Non-conventional amino acid | Code |
|---|---|---|---|
| aminocyclopropane-carboxylateXXX | Cpro XXX | L-N-methylasparagine | Nmasn |
| aminoisobutyric acid | Aib | L-N-methylaspartic acid | Nmasp |
| aminonorbornyl-CarboxylateXXX | Norb XXX | L-N-methylcysteine | Nmcys |
| | | L-N-methylglutamine | Nmgln |
| cyclohexylalanine | Chexa | L-N-methylglutamic acid | Nmglu |
| cyclopentylalanine | Cpen | L-N-methylhistidine | Nmhis |
| D-alanine | Dal | L-N-methylisoleucine | Nmile |
| D-arginine | Darg | L-N-methylleucine | Nmleu |
| D-aspartic acid | Dasp | L-N-methyllysine | Nmlys |
| D-cysteine | Dcys | L-N-methylmethionine | Nmmet |
| D-glutamine | Dgln | L-N-methylnorleucine | Nmnle |
| D-glutamic acid | Dglu | L-N-methylnorvaline | Nmnva |
| D-histidine | Dhis | L-N-methylornithine | Nmorn |
| D-isoleucine | Dile | L-N-methylphenylalanine | Nmphe |
| D-leucine | Dleu | L-N-methylproline | Nmpro |
| D-lysine | Dlys | L-N-methylserine | Nmser |
| D-methionine | Dmet | L-N-methylthreonine | Nmthr |
| D-ornithine | Dorn | L-N-methyltryptophan | Nmtrp |
| D-phenylalanine | Dphe | L-N-methyltyrosine | Nmtyr |
| D-proline | Dpro | L-N-methylvaline | Nmval |
| D-serine | Dser | L-N-methylethylglycine | Nmetg |
| D-threonine | Dthr | L-N-methyl-t-butylglycine | Nmtbug |
| D-tryptophan | Dtrp | L-norleucine | Nle |
| D-tyrosine | Dtyr | L-norvaline | Nva |
| D-valine | Dval | α-methyl-aminoisobutyrate | Maib |
| D-α-methylalanine | Dmala | α-methyl-γ-aminobutyrate | Mgabu |
| D-α-methylarginine | Dmarg | α-methylcyclohexylalanine | Mchexa |
| D-α-methylasparagine | Dmasn | α-methylcyclopentylalanine | Mcpen |
| D-α-methylaspartate | Dmasp | α-methyl-α-napthylalanine | Manap |
| D-α-methylcysteine | Dmcys | α-methylpenicillamine | Mpen |
| D-α-methylglutamine | Dmgln | N-(4-aminobutyl)glycine | Nglu |
| D-α-methylhistidine | Dmhis | N-(2-aminoethyl)glycine | Naeg |
| D-α-methylisoleucine | Dmile | N-(3-aminopropyl)glycine | Norn |
| D-α-methylleucine | Dmleu | N-amino-α-methylbutyrate | Nmaabu |
| D-α-methyllysine | Dmlys | α-napthylalanine | Anap |
| D-α-methylmethionine | Dmmet | N-benzylglycine | Nphe |
| D-α-methylornithine | Dmorn | N-(2-carbamylethyl)glycine | Ngln |
| D-α-methylphenylalanine | Dmphe | N-(carbamylmethyl)glycine | Nasn |
| D-α-methylproline | Dmpro | N-(2-carboxyethyl)glycine | Nglu |
| D-α-methylserine | Dmser | N-(carboxymethyl)glycine | Nasp |
| D-α-methylthreonine | Dmthr | N-cyclobutylglycine | Ncbut |
| D-α-methyltryptophan | Dmtrp | N-cycloheptylglycine | Nchep |
| D-α-methyltyrosine | Dmty | N-cyclohexylglycine | Nchex |
| D-α-methylvaline | Dmval | N-cyclodecylglycine | Ncdec |
| D-α-methylalnine | Dnmala | N-cyclododeclglycine | Ncdod |
| D-α-methylarginine | Dnmarg | N-cyclooctylglycine | Ncoct |
| D-α-methylasparagine | Dnmasn | N-cyclopropylglycine | Ncpro |
| D-α-methylasparatate | Dnmasp | N-cycloundecylglycine | Ncund |
| | | N-(2,2-diphenylethyl)glycine | Nbhm |
| D-α-methylcysteine | Dnmcys | N-(3,3-diphenylpropyl)glycine | Nbhe |
| D-N-methylleucine | Dnmleu | N-(3-indolylethyl) glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nva |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |

TABLE 2-continued

Non-conventional or modified amino acids.

| Non-conventional amino acid | Code | Non-conventional amino acid | Code |
|---|---|---|---|
| L-α-methylisoleucine | Mile | N-(2-methylthioethyl)glycine | Nmet |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl)glycine | Nser |
| D-N-methylisoleucine | Dnmile | N-(imidazolylethyl)glycine | Nhis |
| D-N-methylleucine | Dnmleu | N-(3-indolylethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | mser | L-α-methylthreonine | Mthr |
| L-α-methylvaline | Mtrp | L-α-methyltyrosine | Mtyr |
| L-α-methylleucine | Mval Nnbhm | L-N-methylhomophenylalanine | Nmhphe |
| N-(N-(2,2-diphenylethyl)carbamylmethyl-glycine | Nnbhm | N-(N-(3,3-diphenylpropyl)carbamylmethyl(1)glycine | Nnbhe |
| 1-carboxy-1-(2,2-diphenylethylamino)cyclopropane | Nmbc | XXX | XXX |

According to a presently preferred embodiment of the invention, the antioxidant compound has the general formula:

A-Y1-Cys-Y2-Cys-Y3-B wherein, Cys is a cysteine residue, A is the first hydrophobic or non-charged moiety; B is the second hydrophobic or non-charged moiety; Y1, Y2 and Y3 are each individually one or more amino acid residues in the range of 0-30, preferably 0-20, more preferably 0-10, most preferably 0-5, 0-4, 0-3, 0-2 or 0-1 amino acid residues, with the provision that Y1, Y2 and Y3 collectively provide for at least two amino acid residues in the peptide.

A compound which has the above listed properties and which is hydrolyzable within a cell so as to generate a plurality of antioxidant species acting in concert is for example:

(SEQ ID NO: 2)
A-Cys-A1-A2-Cys-B wherein A1 and A2 are amino acid residues. This tetra-peptide having hydrophobic or non-charged moieties (A and B) at the N and C terminals and which is an antioxidant by itself, is hydrolyzable in vivo to yield additional 14 antioxidant species, each having at least one cysteine residue, each of which is active in effecting antioxidation by virtue of the functional $CH_2$—SH-group of the cysteine residue thereof:

1. A-Cys (SEQ ID NO: 3)

2. A-Cys-A1 (SEQ ID NO: 4)

3. A-Cys-A1-A2 (SEQ ID NO: 5)

4. A-Cys-A1-A2-Cys (SEQ ID NO: 6)

5. Cys-A1-A2-Cys-B (SEQ ID NO: 7)

6. A1-A2-Cys-B (SEQ ID NO: 8)

7. A2-Cys-B (SEQ ID NO: 9)

8. Cys-B (SEQ ID NO: 10)

```
 9. Cys-A1-A2-Cys                        (SEQ ID NO: 11)

10. Cys-A1-A2                            (SEQ ID NO: 12)

11. Cys-A1                               (SEQ ID NO: 13)

12. Cys                                  (SEQ ID NO: 14)

13. A1-A2-Cys                            (SEQ ID NO: 15)

14. A2-Cys                               (SEQ ID NO: 16)
```

A specific example of an A-Cys-A1-A2-Cys-B (SEQ ID NO:2) tetrapeptide antioxidant compound is N-Acetyl Cysteine-Glycine-Proline-Cysteine-Amid (SEQ ID NO:1), which compound is designated in the Examples section that follows as CB and has the following chemical structure:

$CH_3CO-NH-CH(CH_2SH)CO-NHCH_2CO-N(CH_2-CH_2-CH_2)-CO-NH-CH(CH_2SH)-CO-NH_2$

Another compound which has the above listed properties and which is hydrolyzable within a cell so as to generate a plurality of antioxidant species acting in concert is for example the tripeptide having the general formula:

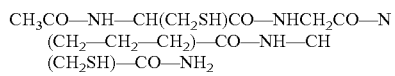
```
    A-Cys-A1-Cys-B                       (SEQ ID NO: 17)
```

This tripeptide can be hydrolyzed in vivo to yield an additional 9 species, each having at least one cysteine residue which is active in effecting antioxidation by virtue of the functional $CH_2$—SH-group thereof:

```
 1. A-Cys                                (SEQ ID NO: 3)

2. A-Cys-A1                             (SEQ ID NO: 4)

3. A-Cys-A1-Cys                         (SEQ ID NO: 18)

4. Cys-A1-Cys-B                         (SEQ ID NO: 19)

5. Cys-A1-Cys                           (SEQ ID NO: 20)

6. A1-Cys                               (SEQ ID NO: 21)

7. Cys-A1                               (SEQ ID NO: 13)

8. Cys-B                                (SEQ ID NO: 10)

9. Cys                                  (SEQ ID NO: 14)
```

It will be appreciated in this respect that living cells include a repertoire of peptidases capable of hydrolyzing a peptide bond formed between any pair of amino acid residues in a peptide. Some peptidases are more specific than others, they may have different abundancy and subcellular distribution, so as to result in some antioxidant species being more represented than others in a certain cellular environment.

To successfully protect biological systems from oxidants, the antioxidant must have a higher reactivity for the oxidant than the biologic molecule which it seeks to protect. To protect the desired biologic system from oxidation, it is also necessary for the antioxidant to partition itself adjacent to the molecule to be protected. As an example, a molecule to be protected within the lipid bilayer of plasma, endosomal or nuclear membranes might be best protected by an antioxidant with, at least in part, a lipophilic structure, so that it is partitioned to or near the lipid portion of the membrane, adjacent to the molecule needing protection from oxidation.

The hydrophobic or non-charged moieties conjugated to the antioxidant peptides of the present invention can be of any type which will render the compound sufficiently hydrophobic or non-charged so as to penetrate into the cytoplasm via its membrane miscibility properties. The exact type will of course depend on the peptide itself, as some peptides are more hydrophobic or non-charged than others. For central nervous system and other applications the compound of the present invention should be designed sufficiently hydrophobic or non-charged so as to cross blood barriers, such as, BBB, blood retinal barrier and blood testis barrier.

In addition to peptidases, living cells are also characterized by a large repertoire of other hydrolases such as, but not limited to, esterases and amidases, which are effective in hydrolyzing the bonds between the hydrophobic or non-charged moieties A and/or B and the peptide in-between, so as to increase the repertoire of antioxidant species released inside the cell. This cleavage action has an additional effect. Removal of one or both of the hydrophobic or non-charged moieties results in decrease in the total hydrophobic or non-charged moiety of the antioxidant species thus generated and as a result, the formed species are advantageously trapped in the cells, so as to efficiently exert their antioxidant properties therein.

Thus, according to a preferred embodiment of the present invention cleavage of the first bond and/or the second bond which connect between the hydrophobic or non-charged moieties A and/or B by a cellular hydrolase results in loss of membrane miscibility, therefore the antioxidant species are trapped within the cell so as to exert their antioxidant activity.

Each of the first and second hydrophobic or non-charged moieties can independently be, for example, alkyl, aryl, alkene, arene or cholesteril having a backbone of 1-50 carbon atoms.

As used herein in the specification and in the claims section that follows, the term "alkyl" refers to a saturated aliphatic hydrocarbon group having a linear or branched backbone. Preferably, the alkyl has 1 to 20 carbon atoms in its backbone. Whenever a numerical range, e.g., "1-20", is stated herein, it means that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, it is a lower alkyl having 1 to 4 carbon atoms. The alkyl group may be substituted or unsubstituted. When substituted, the substituent group can be, for example, cycloalkyl, aryl, heteroaryl, heteroalicyclic, hydroxy, alkoxy, aryloxy, thiohydroxy, thioalkoxy, thioa, cyano, halo, carbonyl, thiocarbonyl, O-carbamyl, N-carbamyl, O-thiocarbamyl, N-thiocarbamyl, C-amido, N-amido, C-carboxy, O-carboxy, nitro, sulfonamido, trihalomethanesulfonamido, silyl, guanyl, guanidino, ureido, amino or $NR_{10}R_{11}$, wherein $R_{10}$ and $R_{11}$ are each independently hydrogen, alkyl, cycloalkyl, aryl, carbonyl, sulfonyl, trihalomethysulfonyl and, combined, a five- or six-member heteroalicyclic ring.

A "cycloalkyl" group refers to an all-carbon monocyclic or fused ring (i.e., rings which share an adjacent pair of carbon atoms) group wherein, one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, aryl, heteroaryl, heteroalicyclic, hydroxy, alkoxy, aryloxy, thiohydroxy, thioalkoxy, thioaryloxy, cyano, halo, carbonyl, thiocarbonyl, C-carboxy, O-carboxy, O-carbamyl, N-carbamyl, C-amido, N-amido, nitro, amino and $NR_{10}R_{11}$ as defined above.

An "alkenyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, halo, trihalomethyl, alkyl, hydroxy, alkoxy, aryloxy, thiohydroxy, thiocarbonyl, C-carboxy, O-carboxy, O-carbamyl, N-carbamyl, O-thiocarbamyl, N-thiocarbamyl, C-amido, N-amido, sulfinyl, sulfonyl, amino and $NR_{10}R_{11}$ as defined above.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, halo, trihalomethyl, hydroxy, alkoxy, aryloxy, thiohydroxy, thiocarbonyl, sulfonamido, C-carboxy, O-carboxy, sulfinyl, sulfonyl, O-carbamyl, N-carbamyl, O-thiocarbamyl, N-thiocarbamyl, C-amido, N-amido, amino or $NR_{10}R_{11}$ as defined above.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, alkyl, cycloalkyl, aryl, heteroaryl, halo, trihalomethyl, hydroxy, alkoxy, aryloxy, thiohydroxy, thioalkoxy, thioaryloxy, cyano, nitro, carbonyl, thiocarbonyl, C-carboxy, O-carboxy, O-carbamyl, N-carbamyl, O-thiocarbamyl, N-thiocarbamyl, sulfinyl, sulfonyl, C-amido, N-amido, amino and $NR_{10}R_{11}$ as defined above.

According to a presently most preferred embodiment of the present invention, each of the hydrophobic or non-charged moieties identified herein by A and B, is independently N-acetyl, tert butyl, isopropyl, n-butyl, n-pentyl, amide or ester.

A compound according to the present invention can be administered per se to an organism, such as a human being or any other mammal, or in a pharmaceutical composition where it is mixed with suitable carriers or excipients.

Thus, according to another aspect of the present invention there is provided a pharmaceutical composition for preventing or reducing oxidative stress, the composition comprising a pharmaceutically acceptable carrier and, as an active ingredient, an antioxidant compound as described hereinabove.

As used herein a "pharmaceutical composition" refers to a preparation of one or more of the compounds described herein, or physiologically acceptable salts or prodrugs thereof, with other chemical components such as physiologically suitable carriers and excipients. The purpose of a pharmaceutical composition is to facilitate administration of a compound to an organism.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

Pharmaceutical compositions may also include one or more additional active ingredients, such as, but not limited to, anti-inflammatory agents, antimicrobial agents, anesthetics in addition to the antioxidant compounds.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active compounds into preparations which can be used pharmaceutically. Proper formulation is dependent upon the route of administration chosen.

For injection, the compounds of the invention may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical compositions for parenteral administration include aqueous solutions of the active preparation in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile, pyrogen-free water, before use.

The compounds of the present invention may also be formulated in rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions suitable for use in context of the present invention include compositions wherein the active ingredients are contained in an amount effective to achieve the intended purpose. More specifically, a therapeutically effective amount means an amount of antioxidant preparation effective to prevent, alleviate or ameliorate symptoms of disease or prolong the survival of the subject being treated.

Determination of a therapeutically effective amount is well within the capability of those skilled in the art, especially in light of the detailed disclosure provided herein.

Toxicity and therapeutic efficacy of the compounds described herein can be determined by standard pharmaceutical procedures in cell cultures or experimental animals, e.g., by determining the $IC_{50}$ and the $LD_{50}$ (lethal dose causing death in 50% of the tested animals) for a subject compound. The data obtained from these cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. See e.g., (54).

Depending on the severity and responsiveness of the condition to be treated, dosing can also be a single administration of a slow release composition, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

The present invention can be used to treat any one of a plurality of diseases, disorders or conditions associated with the formation of oxidative stress.

As used herein, the term "treat" include substantially inhibiting, slowing or reversing the progression of a disease, disorder or condition, substantially ameliorating clinical symptoms of a disease disorder or condition, or substantially preventing the appearance of clinical symptoms of a disease, disorder or condition.

The compounds of the present invention can be used to treat non-central nervous system disorders such as rheumatoid arthritis, cataract, Down syndrome, cystic fibrosis, diabetes, acute respiratory distress syndrome, asthma, post-surgical neurological dysfunction, amyotrophic lateral sclerosis, atherosclerotic cardiovascular disease, hypertension, post-operative restenosis, pathogenic vascular smooth muscle cell proliferation, pathogenic intra-vascular macrophage adhesion, pathogenic platelet activation, pathogenic lipid peroxidation, myocarditis, stroke, multiple organ dysfunction, complication resulting from inflammatory processes, AIDS, cancer, aging, bacterial infection, sepsis; viral disease, such as AIDS, hepatitis C, an influenza and a neurological viral disease, all of which were previously shown to be associated with the formation and/or overproduction of oxidants and habits resulting in oxidative stress, such as, but not limited to, smoking, sun tanning, cancer treatment, radiation cocaine consumption and morphine consumption.

The compounds of the present invention can also be used to treat a central nervous system disorder characterized by oxidative stress, such as, neurodegenerative disorders, Parkinson's disease, Alzheimer's disease, Creutzfeldt-Jakob disease, cerebral ischemia, multiple sclerosis, degenerative diseases of the basal ganglia, motoneuron diseases, scrapies, spongiform encephalopathy, neurological viral diseases, motoneuron diseases, post-surgical neurological dysfunction and loss or memory impairment, all of which were previously shown to be associated with the formation and/or overproduction of oxidants and habits resulting in oxidative stress, such as, but not limited to, smoking, sun tanning, cancer treatment, radiation cocaine consumption and morphine consumption.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Example 1

Synthesis of N-Acetyl Cysteine-Glycine-Proline-Cysteine-Amid

The synthesis of N-Acetyl Cysteine-Glycine-Proline-Cysteine-Amid (CB, SEQ ID NO:1) having the chemical structure of: $CH_3CO—NH—CH(CH_2SH)CO—NHCH_2CO—N(CH_2—CH_2—CH_2)CH—CO—NH—CH(CH_2SH)—CO—NH_2$ (molecular weight of 406) is described herein.

Synthesis:

CB was prepared by solid phase synthesis of peptides according to published protocols. The synthesis was carried out according to Fastmoc 0.25 mmol modules in a peptide synthesizer Model 433A (Applied Biosystems) according to the User's manual.

In particular, 9-fluorenylmethoxycarbonyl (Fmoc) amino acid (1 mmol) was dissolved and activated in the cartridge in a mixture of 3.0 g of 0.45 M 2-(1H-benzoltriazol-1-yl)-1,1,3,3-tetramethyluronium hexafluorophosphate (HBTU/HOBt) in DMF, 2 M Diisopropyethylamine (DIEA) and 0.8 ml N-methyl-pyrrolidone (NMP). De-protection was carried out in 22% piperidine solution in NMP. All steps were carried out under nitrogen.

De-Protection:

The resin was de-protected as follows: Fmoc-Benzhydrylamine resin (368 mg; 0.25 mmol) was stirred in N-methylpyrrolidone (7 ml). De-protection was carried out by washing the resin with 22% piperidine/NMP solution for 2 minutes. The solvents were removed and the resin was subjected to a second treatment with 22% piperidine/NMP for 7.6 minutes. Then, the resin was washed 6 times with DCM, followed by 4 washes in NMP.

Step 1:

Fmoc-trityl cysteine (0.454 g) was reacted for 6 min in NMP (2 g) together with 0.9 mmol of 0.45M HPTU/HOBt in DMF (2 g). De-protection was carried out as outlined above.

Step 2:

Fmoc-proline (0.478 g) was reacted for 6 min in NMP (2 g) together with 0.9 mmol of 0.45 M HPTU/HOBt in DMF (2 g). De-protection was carried out as outlined above.

Step 3:

Fmoc-glycine (0.493 mg) was reacted for 6 min in NMP (2 g) together with 0.9 mmol of 0.45 HPTU/HOBt in DMF (2 g). De-protection was carried out as outlined above.

Step 4:

Fmoc-trityl cysteine (0.454 g) was reacted for 6 min in NMP (2 g) together with 0.9 mmol of 0.4 5M HPTU/HOBt in DMF (2 g). De-protection was carried out as outlined above.

Step 5:

Acetic anhydride (0.534 g) was reacted 6 min in NMP (2 g) together with 0.9 mmol of 0.45M HPTU/HOBt in DMF (2 g).

Step 6:

The resin was mixed using a vortex with 95% TFA/2.5% DDW/2.5% triisopropyl silane for 10 min at 40° C. and 2 hours at room temperature. The mixed resin was filtered and the resulting peptide was precipitated with cold ether. The precipitate was washed 4 times with cold ether, next 10% acetic acid was added followed by lyophilization.

The yield of the above synthesis was 80 mg of the CB molecule.

Analysis:

The product of the above synthesis was analyzed by HPLC. The HPLC profile of the purified CB compound is presented in FIG. 1. Mass spectra of CB is 419.9. Amino acid data: is Gly—retention time of 13.35 min; 401.023 nmol/ml; Pro—retention time of 20.83 min; 402.56 nmole/ml; Cys—degraded.

Example 2

Inhibition of JNK (c-Jun $NH_2$-Terminal Kinase) and p38 Enzymes

In order to show the efficacy of CB against a stimulant that activates oxidative stress, an inhibition assay of both JNK (c-Jun NH2-terminal kinase) and p38 enzymes in tissue culture was performed.

NIH3T3 cells overexpressing EGF receptor (DHER14 cells) (55) were exposed to cisplatin (CDDP, 30 μM) which activates specific enzymes involved in apoptosis including JNK and p38.

Figure 2:
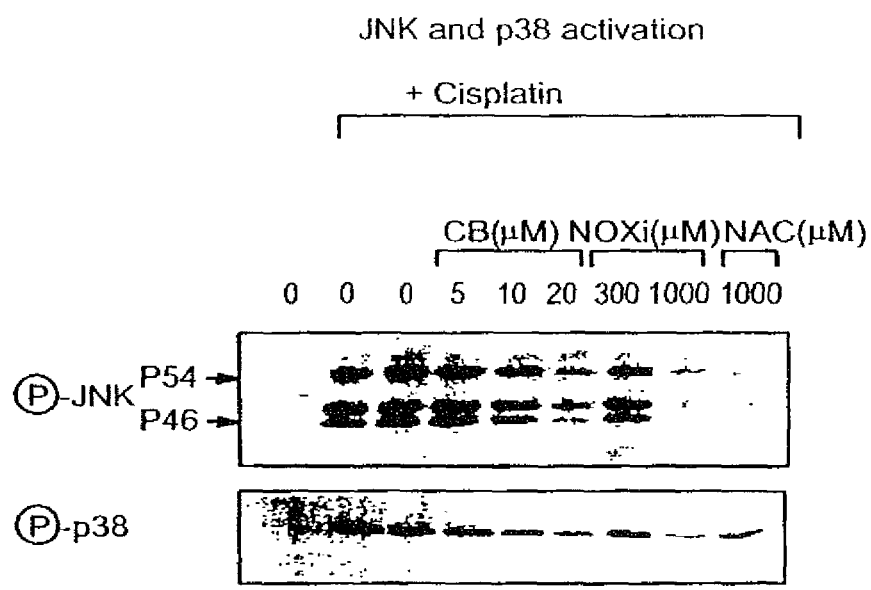
FIG. 2 shows inhibition of JNK and p38 phosphorylation by CB, NOXi and NAC as determined by immunoprecipitation with specific antibodies against phosphorylated JNK and p38 followed by gel electrophoresis.

As shown in FIG. 2, JNK or p38 were detected by specific antibodies essentially as previously described (6). In the presence of increasing concentrations of CB, a dramatic reduction in the phosphrylated form of either p38 or JNK enzymes was obtained. In the presence of 20 μM CB, phosphorylated p38 and JNK enzymes were not detected at all. Two known antioxidants were used as positive controls, NOXi (at 300 and 1000 μM) and NAC (NAC) (at 1000 μM). The efficacy of CB at 20 μM was similar to that obtained by the addition of 1 mM of N-acetyl cysteine.

Example 3

Inhibition of ROS Production

Figure 3:
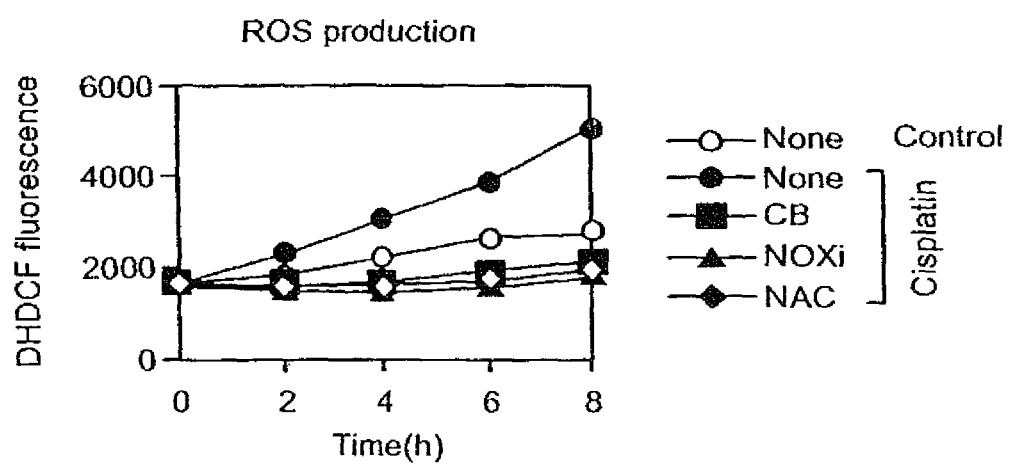
FIG. 3 represents cellular ROS levels as determined using a fluorescence assay in the presence of CB, NOXi and NAC antioxidants.

The concentration of reactive oxygen species (ROS) in DHER14 cells following administration of antioxidants was determined using the ROS sensitive fluorescent dye DHDCF (fluoresceine derivative). As shown in FIG. 3, reduction of ROS below normal levels was prominent in the presence of 20 μM of CB. Two known antioxidants were used as control, NOXi (at 1000 μM) and NAC (NAC) (at 1000 μM). The efficacy of CB in reducing ROS was about ~50 fold better then these two known antioxidants. Thus, at 20 μM CB was as efficient as 1000 μM NAC or 1000 μM NOXi.

REFERENCES CITED

1. D'Angio C T, Finkelstein J N. Oxygen regulation of gene expression: a study in opposites. Mol Genet Metab 2000 September-October; 71(1-2):371-80. (1996).
2. Schoonbroodt S, Piette J. (2000) Oxidative stress interference with the nuclear factor-kappa B activation pathways. *Biochem Pharmacol* 60(8):1075-83.
3. Buttke T M, Sandstrom P A. Oxidative stress as a mediator of apoptosis. Immunol Today 1994 January; 15(1):7-10.
4. Jacobson M D. Reactive oxygen species and programmed cell death. Trends Biochem Sci 1996 March; 21(3): 83-6.
5. Tournier C, Hess P, Yang D D, Xu J, Turner T K, Nimnual A, Bar-Sagi D, Jones S N, Flavell R A, Davis R J. Requirement of JNK for stress-induced activation of the cytochrome c-mediated death pathway. Science 2000 May 5; 288(5467): 870-4.
6. Saitoh M, Nishitoh H, Fujii M, Takeda K, Tobiume K, Sawada Y, Kawabata M, Miyazono K, Ichijo H. Mammalian thioredoxin is a direct inhibitor of apoptosis signal-regulating kinase (ASK) 1. EMBO J. 1998 17:2596-606.

7. Craig. C. Transcend therapeutics takes flight against oxidative stress public. BioWorld Today. Aug. 27, 1996, pp. 1-2.

8. Jenner, O. Oxidative damage in neurodengenerative disease. Lancet, 344, 796-798 (1994).

9. Olanow, C. W. A. radical hypothesis for neurodegeneration. Trends. Neurol. Soc. 16, 439-444 (1993).

10. Jones D C, Gunasekar P G, Borowitz J L, Isom G E. Dopamine-induced apoptosis is mediated by oxidative stress and is enhanced by cyanide in differentiated PC12 cells. J Neurochem 74, 2296-2304 (2000).

11. Olanow, C. W. Oxidation reactions in Parkinson's disease. Neurology 40, 32-37 (1990).

12. Fahn S. & Cohen, G. The oxidant stress hypothesis in Parkinson's disease: evidence supporting it. Ann Neurol. 32, 804-812 (1992).

13. Nunomura A, Perry G, Hirai K, Aliev G, Takeda A, Chiba S, Smith M A. Neuronal RNA oxidation in Alzheimer's disease and Down's syndrome. Ann N Y Acad. Sci. 893, 362-4. (1999a).

14. Nunomura A, Perry G, Pappolla M A, Wade R, Hirai K, Chiba S, Smith M A. RNA oxidation is a prominent feature of vulnerable neurons in Alzheimer's disease. J. Neurosci. 19, 1959-1964 (1999b).

15. Thomas, T., Thomas, G. M., McLendon, C., Sutton, T. & Mullan, M. β-Amyloid-mediated vasoactivity and vascular endothelial damage. Nature 380, 168-171 (1996).

16. Brown, D. R., Schmidt, B. & Kretzschmar, H. A. Role of microglia and host prion protein in neurotoxicity of a prion protein fragment. Nature 380, 345-347.

17. Mann C L, Davies M B, Boggild M D, Alldersea J, Fryer A, Jones P W, Ko K o C, Young C, Strange R C, Hawkins C P. Glutathione S-transferase polymorphisms in MS: their relationship to disability. Neurology 54, 552-557 (2000)

18. Cafe, C., Toni, C., Betorelli, L., Angeretti, N., Luccan E., Forloni, G., & Marzatico, F., Oxidative stress after acute and chronic application of b-amyloid fragment 25-35 in cortical cultures. Neuroscience Letts. 203, 61-65 (1996).

19. Raina A K, Takeda A, Nunomura A, Perry G, Smith M A. Genetic evidence for oxidative stress in Alzheimer's disease. Neuroreport. 10, 1355-1357 (1999).

20. Rottkamp C A, Nunomura A, Raina A K, Sayre L M, Perry G, Smith M A Oxidative stress, antioxidants, and Alzheimer disease. Alzheimer Dis Assoc Disord 14 Suppl 1:S62-6 (2000).

21. Penkowa M, Hidalgo J. (2001) Metallothionein treatment reduces proinflammatory cytokines IL-6 and TNF-α and apoptotic cell death during experimental autoimmune encephalomyelitis (EAE). Exp Neurol. 170(1):1-14.

22. Espejo C, Carrasco J, Hidalgo J, Penkowa M, Garcia A, Saez-Torres I, Martinez-Caceres E M. (2001) Differential expression of metallothioneins in the CNS of mice with experimental autoimmuneencephalomyelitis. *Neuroscience.* 105(4):1055-65.

23. Liu Y, Zhu B, Luo L, Li P, Paty D W, Cynader M S (2001a) Heme oxygenase-1 plays an important protective role in experimentalautoimmune encephalomyelitis. *Neuroreport;* 12(9): 1841-5

24. Peiro C, Lafuente N, Matesanz N, Cercas E, Llergo J L, Vallejo S, Rodriguez-Manas L, Sanchez-Ferrer C F. (2001) High glucose induces cell death of cultured human aortic smooth muscle cells through the formation of hydrogen peroxide. *Br J Pharmacol* 133(7):967-974.

25. Kowluru R A, Tang J, Kern T S. (2001) Abnormalities of retinal metabolism in diabetes and experimental galactosemia. VII. Effect of long-term administration of antioxidants on the development of retinopathy. *Diabetes* 50(8): 1938-42

26. Coppey L J, Gellett J S, Davidson E P, Dunlap J A, Lund D D, Yorek M A. (2001) Effect of antioxidant treatment of streptozotocin-induced diabetic rats on endoneurial blood flow, motor nerve conduction velocity, and vascular reactivity of epineurial arterioles of the sciatic nerve. *Diabetes* 50(8): 1927-37.

27. Harding J. (1991) In *Cataract*. Biochemistry, epidemiology and Pharmacology. Pp. 125-217 Chapman &Hall Lomdom UK.

28. Dudek E J, Shang F, Taylor A. (2001). $H_2O_2$-mediated oxidative stress activates NF-kappaB in lens epithelial cells. Free *Radic Biol Med*. September 1; 31(5):651-8.

29. Akaike T (2001) Role of free radicals in viral pathogenesis and mutation are key molecules in the pathogenesis of various infectious diseases. *Rev Med Virol* March-April; 11(2):87-101

30. Lin C, Zimmer S G, Lu Z, Holland R E Jr, Dong Q, Chambers T M (2001) The involvement of a stress-activated pathway in equine influenza virus-mediated apoptosis. *Virology* August 15; 287(1):202-13

31. Gong G, Waris G, Tanveer R, Siddiqui A. (2001) Human hepatitis C virus NS5A protein alters intracellular calcium levels, induces oxidative stress, and activates STAT-3 and NF-kappa B. *Proc Natl Acad Sci USA* 98(17):9599-604.

32. Goto T, Baba T, Honma K, Shibata Y, Arai Y, Uozumi H, Okuda T. (2001) Magnetic resonance imaging findings and postoperative neurologic dysfunction in elderly patients undergoing coronary artery bypass grafting. *Ann Thorac Surg.*
72(1):137-42.

33. Khan N E, De Souza A C, Pepper J R. (2001) S100 protein: its use as a marker of cerebral damage in cardiac operations. *Ann Thorac Surg.* 72(2):666-7.

34. Reid K H, Li G Y, Payne R S, Schurr A, Cooper N G. (2001). The mRNA level of the potassium-chloride cotransporter KCC2 covaries with seizure susceptibility in inferior colliculus of the post-ischemic audiogenic seizure-prone rat. *Neurosci Lett.* 308(1):29-32.

35. Maulik N, Yoshida T.(2000) Oxidative stress developed during open heart surgery induces apoptosis: reduction of apoptotic cell death by ebselen, a glutathione peroxidase mimic. *J Cardiovasc Pharmacol;*36(5):601-8

36. Maytin M, Leopold J, Loscalzo J. (1999) Oxidant stress in the vasculature. *Curr Atheroscler Rep* 1(2): 156-64.

37. Wagberg M, Jansson A H, Westerlund C, Ostlund-Lindqvist A M, Sarnstrand B, Bergstrand H, Pettersson K. (2001) N,n'-diacetyl-1-cystine (dinac), the disulphide dimer of NAC, inhibits atherosclerosis in whhl rabbits: evidence for immunomodulatory agents as a new approach to prevent atherosclerosis. *J Pharmacol Exp Ther* 299(1):76-82.

38. Cui J, Liu P K. (2001) Neuronal NOS Inhibitor That Reduces Oxidative DNA Lesions and Neuronal Sensitivity Increases the Expression of Intact c-fos Transcripts after Brain Injury. *J Biomed Sci.* 8(4):336-41.

39. Sinha J, Das N, Basu M K.(2001) Liposomal antioxidants in combating ischemia-reperfusion injury in rat brain. *Biomed Pharmacother;*55(5):264-71.

40. Liu P K, Grossman R G, Hsu C Y, Robertson C S. (2001b) Ischemic injury and faulty gene transcripts in the brain. *Trends Neurosci*24 (10):581-8

41. Crack P J, Taylor J M, Flentjar N J, de Haan J, Hertzog P, Iannello R C, Kola I. (2001) Increased infarct size and exacerbated apoptosis in the glutathione peroxidase-1 (Gpx- 1) knockout mouse brain in response to ischemia/reperfusion injury. *J. Neurochem.* 78 (6): 1389-99.

42. Fleshner N E, Klotz L H. Diet, androgens, oxidative stress and prostate cancer susceptibility. Cancer Metastasis Rev 1998-99; 17(4):325-30.

43. The Parkinson Study Group. Effects of tocopherol and deprenyl on the progression of disability in early Parkinson's disease. N. Eng. J. Med. 328, 176-183 (1993).

44. Offen, D., Ziv, I., Srernin, H., Melamed, E. and Hochman, A. Prevention of dopamine-induced cell death by thiol-antioxidants: Possible implications for treatment of Parkinson's disease. Exptt. Neurol., 141, 32-39 (1996).

45. Atlas D., Melamed E. and Ofen D. Brain targeted low molecular weight hydrophobic antioxidant compounds. 1999. U.S. Pat. No. 5,874,468.

46. Watanabe T, Pakala R, Katagiri T, Benedict C R. (2001) Lipid peroxidation product 4-hydroxy-2-nonenal acts synergistically with serotonin in inducing vascular smooth muscle cell proliferation. *Atherosclerosis* 155(1):37-44.

47. Pettersen R J, Kuiper K K, Froyland L, Berge R K, Nordrehaug J E. (2001). Long-term retention of a novel antioxidant sulphur-substituted fatty acid analogue after local delivery in porcine coronary arteries. *Scand Cardiovasc J.;*35 (2):101-6.

48. Bundy, G. L., Ayer, D. E., Banitt, L. S., Belonga, K. L., Mizsak, S. A., Palmer, J. R., Tustin, J. M., Chin, J. E., Hall, E. D., Linseman, K. L., et al. Synthesis of novel 2,4-diaminopyrrolo-[2,3-d]pyrimidines with antioxidant, neuroprotective, and anti asthma activity. J Med. Chem. 38, 4161-3 (1995).

49. Kim G W, Lewen A, Copin J, Watson B D, Chan P H. (2001) The cytosolic antioxidant, copper/zinc superoxide dismutase, attenuates blood-brain barrier disruption and oxidative cellular injury after photothrombotic cortical ischemia in mice. *Neuroscience.* 105 (4): 1007-1018.

50. Yang G Y, Pang L, Ge H L, Tan M, Ye W, Liu X H, Huang F P, Wu D C, Che X M, Song Y, Wen R, Sun Y. (2001) Attenuation of ischemia-induced mouse brain injury by SAG, a redox-inducible antioxidant protein. *J Cereb Blood Flow Metab.* 21(6):722-33.

51. Kosano H, Watanabe H, Nishigori H. (2001) Suppressive effects of thyroxine on glucocorticoid (gc)-induced metabolic changes and cataract formation on developing chick embryos. *Exp Eye Res.* 72(6):643-8.

52. Keles M S, Taysi S, Sen N, Aksoy H, Akcay F. Effect of corticosteroid therapy on serum and CSF malondialdehyde and antioxidant proteins in multiple sclerosis. Can J Neurol Sci 2001 May; 28(2):141-3.

53. Quantitative Drug Design, C. A. Ramsden Gd., Chapter 17.2, F. Choplin Pergamon Press (1992).

54. Fingl, et al., 1975, in "The Pharmacological Basis of Therapeutics", Ch. 1p. 1.

55. Dull T J, Lax I, Schlessinger J, Ullrich A. HER2 cytoplasmic domain generates normal mitogenic and transforming signals in a chimeric receptor. EMBO J. (1989) 8167-73.

What is claimed is:

1. A method of reducing oxidative stress in a subject, the method comprising locally or systemically administering to the subject an antioxidant compound having a general formula of:

N-acetyl-Cys-A1-Cys-amide wherein Cys is an L-cysteine residue, and A1 is an amino acid residue selected from the group consisting of L-alanine, L-arginine, L-asparagine, L-aspartic acid, L-cysteine, L-glutamine, L-glutamic acid, glycine, L-histidine, L-isoleucine, L-leucine, L-lysine, L-methionine, L-phenylalanine, L-proline, L-serine, L-threonine, L-tryptophan, L-tyrosine and L-valine.

2. The method of claim 1, wherein the subject is afflicted with a central nervous system disease associated with formation of oxidative stress or a non-central nervous system disease associated with formation of oxidative stress.

3. The method of claim 2, wherein said non-central nervous system disease is asthma.

4. A method of reducing oxidative stress in a subject, the method comprising locally or systemically administering to the subject an antioxidant compound having the formula:

N-acetyl-Cys-Pro-Cys-amide, wherein Cys is an L-cysteine residue and Pro is an L-proline residue.

5. The method of claim 4, wherein the subject is afflicted with a disease associated with formation of oxidative stress.

6. The method of claim 5, wherein said disease is asthma.

* * * * *